United States Patent [19]

Thoro

[11] Plant 4,161

[45] Dec. 6, 1977

[54] ORANGE TREE

[76] Inventor: Andrew Thoro, 5864 SW. 76th St., Miami, Fla. 33143

[21] Appl. No.: 722,591

[22] Filed: Dec. 6, 1976

[51] Int. Cl.[2] ..... A01H 5/03

[52] U.S. Cl. ..... Plt./45

[58] Field of Search ..... Plt./45

*Primary Examiner*—Robert E. Bagwill

*Attorney, Agent, or Firm*—Clarence A. O'Brien; Harvey B. Jacobson

[57] ABSTRACT

This relates to a novel variety of Temple Orange characterized by being seedless.

1 Drawing Figure

1

The present discovery relates to a new variety of Temple Orange Tree. The new characteristics thereof reside in the seedless quality of the fruit, the ease of rind removal and section detachment, the excellent flavor and storing capacities of the fruit up to 2 months.

This orange tree is a new and improved variety which has resulted from definite breeding programs and experiments carried on by me in a grove in Miami, Fla.

The origin of the tree began with the planting of a graft on rough lemon stock in a grove in Miami, Fla., in 1939. Three years later a new variety of fruit was deemed from the fruit which was seedless. Five years later, it was found that one branch of the tree produced seedless fruit. The bud was grafted to the rough lemon stock and three years later resulted in a seedless fruit. The second bud from the tree was again grafted to a rough lemon stock producing seedless fruit once again. A third grafting took place in 1973 again from a third generation and again the fruit produced was seedless.

These grafts resulted in hundreds of progeny trees which have continuously produced seedless Temple oranges.

My new variety has the following characteristics:

*Tree shape.*—Somewhat drooping.
*Size.*—Medium, good vigor.
*Growth.*—Dense; abundant branching and budding.

2

*Flower.*—Size: regular as a Temple orange.
*Season.*—Blooms continuously.
*Leaves.*—As on Temple orange tree.

Fruit: external characteristics:
*Color.*—Mandarin Orange (Maerz & Paul).
*Surface.*—As Temple orange.
*Shape.*—Spheroid, symmetrical.
*Size.*—Base and calyx as Temple orange.
*Stem.*—Apex, navel and aerole as Temple orange.

Fruit: internal characteristics:
Rind, oil glands, oil, glandular layer, mesocarp axis, segments, axis, pulp: as Temple orange.
Juice, ample, color, orange yellow, very sweet, pleasantly acid not bitter, medium aroma, attractive.

The above describes a new variety of Temple orange tree retaining many of the qualities of the original Temple orange tree of Florida with ease of rind removal and section detachment, excellent flavor and the capabilities for shipping and storage.

Having thus disclosed my invention, I claim:

1. A new and distinct variety of Temple orange tree, substantially as described, characterized particularly by the seedless quality of the fruit.

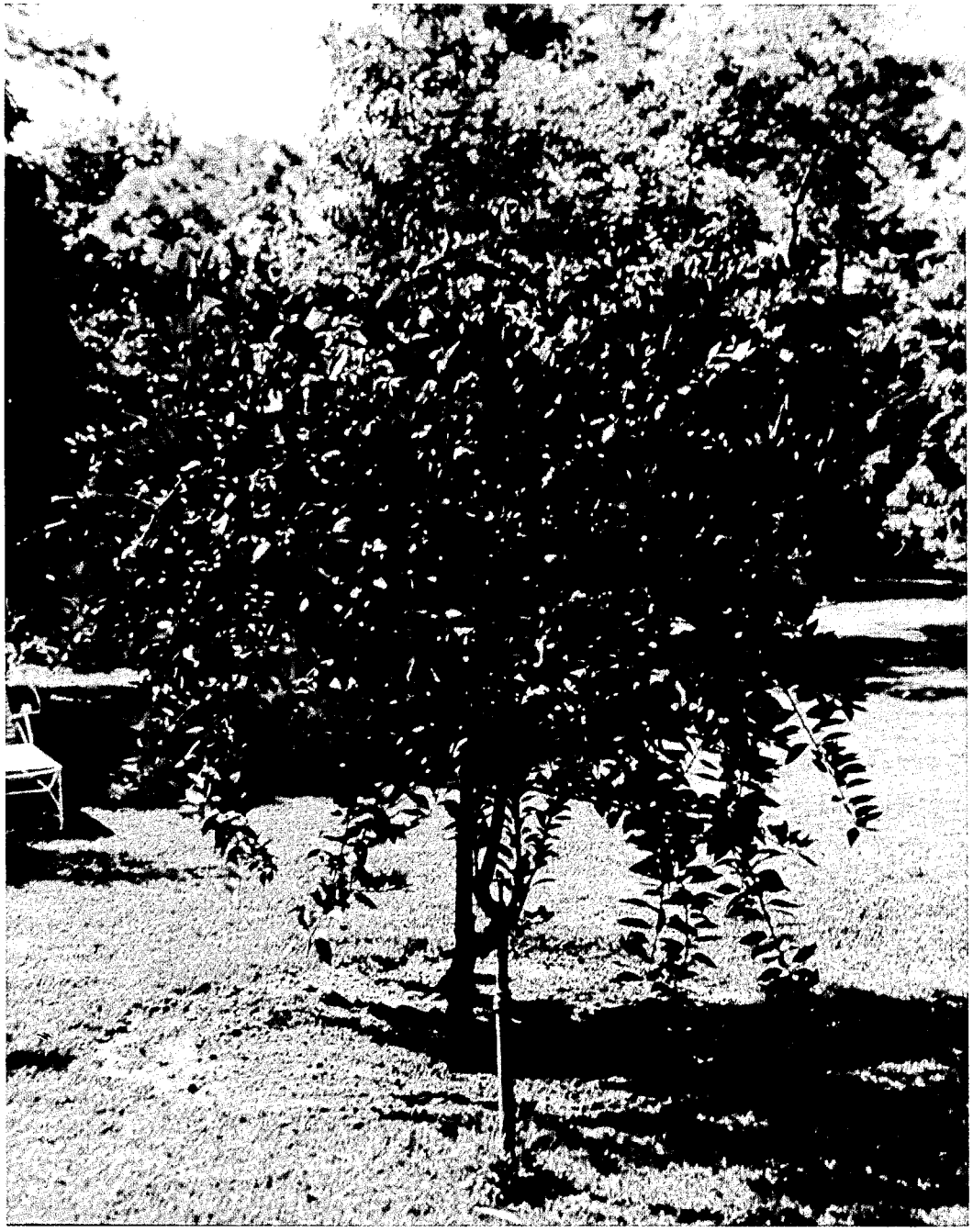

* * * * *